United States Patent [19]

Krabetz et al.

[11] Patent Number: 4,925,823
[45] Date of Patent: May 15, 1990

[54] PROCESS AND CATALYST FOR THE PREPARATION OF METHACRYLIC ACID

[75] Inventors: Richard Krabetz, Kirchheim; Gerd Duembgen, Dannstadt-Schauernheim; Friedbert Nees, Stutensee; Franz Merger, Frankenthal; Gerd Fouquet, Neustadt, all of Fed. Rep. of Germany

[73] Assignee: BASF Aktiengesellschaft, Ludwigshafen, Fed. Rep. of Germany

[21] Appl. No.: 875,516

[22] Filed: Jun. 19, 1986

Related U.S. Application Data

[63] Continuation of Ser. No. 470,947, Mar. 1, 1983, abandoned.

[30] Foreign Application Priority Data

Mar. 10, 1982 [DE] Fed. Rep. of Germany ....... 3208572

[51] Int. Cl.$^5$ .............................................. B01J 27/19
[52] U.S. Cl. .................... 502/211; 502/305; 502/311; 502/316; 502/318; 502/321; 502/338; 502/345; 502/353
[58] Field of Search ............... 502/210, 211, 305, 311, 502/316, 318, 321, 338, 345, 353

[56] References Cited

U.S. PATENT DOCUMENTS

| | | | |
|---|---|---|---|
| 3,965,163 | 6/1976 | Oda et al. | |
| 4,178,464 | 12/1979 | Sakamoto et al. | 252/435 X |
| 4,261,859 | 4/1981 | Khoobriar | 252/437 |
| 4,272,408 | 6/1981 | Daniel | 252/437 |
| 4,334,116 | 6/1982 | Velenyi et al. | 252/435 X |
| 4,335,018 | 6/1982 | Franz et al. | 252/435 |
| 4,444,907 | 4/1984 | Ohdan et al. | 502/210 |
| 4,504,677 | 3/1985 | Sakamoto et al. | 502/211 X |

FOREIGN PATENT DOCUMENTS

| | | | |
|---|---|---|---|
| 55-133329 | 3/1979 | Japan | 252/437 |
| 1430337 | 3/1976 | United Kingdom | 252/435 |
| 1438806 | 6/1976 | United Kingdom | 252/435 |
| 1473035 | 5/1977 | United Kingdom . | |
| 2001256 | 7/1977 | United Kingdom . | |
| 206252 | 3/1979 | United Kingdom . | |
| 2040717 | 9/1980 | United Kingdom . | |

*Primary Examiner*—Anthony McFarlane
*Attorney, Agent, or Firm*—Oblon, Spivak, McClelland, Maier & Neustadt

[57] ABSTRACT

Oxidation catalysts of the general formula

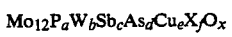

$$Mo_{12}P_aW_bSb_cAs_dCu_eX_fO_x$$

where
X is Nb, Fe, Mn, Sn and/or Cr,
a is 0.1–3,
b is 0.1–4,
c is <0–2,
d is 0–1,
e is 0–1,
d+e is <0–2,
f is 0–1.5,
e+f is 0–2 and
x is the number of oxygen atoms formally required to saturate the valencies of the other catalyst components, may be used particularly advantageously for the preparation of methacrylic acid by gas phase oxidation of methacrolein.

3 Claims, No Drawings

PROCESS AND CATALYST FOR THE PREPARATION OF METHACRYLIC ACID

This application is a continuation of application Serial No. 470,947, filed Mar. 1, 1983, and now abandoned.

Numerous oxidation catalysts, and their use for the preparation of methacrylic acid by gas phase oxidation of methacrolein, have been proposed. However, these catalysts only partially, if at all, meet the requirements for an industrial process in respect of high selectivity, coupled with high methacrolein conversions and high space velocities over long operating periods.

British Patent 2,040,717, for example, discloses catalysts which contain Mo, Cu, P, Sb and Cs and/or Ca. However, these catalysts give an unsatisfactory selectivity of 76% for methacrylic acid formation, at methacrolein conversions of only 75%. British Patent 1,473,035 proposes catalysts which additionally to Mo, Cu and P contain one or more alkali metals and one or more metals selected from the group Sb, V, W, Fe, Mn and Sn. It is true that these catalysts give, in sustained operation, methacrolein conversions of up to 91.5% and selectivities of 82% but the low space velocity of 1,000 $h^{-1}$ and relatively high temperature of 325° C. or more are unsatisfactory for an industrial process. Oxidation catalysts of the type disclosed in British Patent 2,046,252, which contain Mo, P and V, with or without As and Cu or other cationic elements, show, it is true, a high catalytic activity, but only if the catalyst particle size is less than 2 mm—which is undesirable in industrial operation—and if used at the relatively high temperature of 330° C. Oxidation catalysts which are prepared in the presence of high chloride ion concentrations of as much as about 1-5 equivalents per equivalent of molybdenum, for example the catalysts, containing Mo, P and W, of the type disclosed in European Patent Application 0,010,429, or the catalysts, containing Mo, P and Sb, with or without W, disclosed in U.S. Pat. No. 3,965,163, show, it is true, relatively good catalytic activity for short operating periods, but it is difficult to produce reproducibly catalysts of this type which have a long life and are adequately selective. Moreover, the catalysts mentioned tend to give increased formation of acetic acid if they are used in particle sizes which are industrially desirable, namely not less than 3 mm.

British Patent 2,001,256 moreover discloses oxidic catalysts which contain Mo, P, As, Cu and Cr and which are prepared in the presence or absence of a dibasic carboxylic acid, hydroxycarboxylic acid, mannitol or pyrogallol as the reducing agent.

However, the properties of these and the other catalysts mentioned above are generally unsatisfactory if methacrolein which has been prepared by condensing propanal with formaldehyde is used as the raw material in the preparation of methacrylic acid. This methacrolein contains, as impurities attributable to the method of preparation, not only unconverted propanal but also organic amines, dimers of methacrolein and methylpentenal, and even small amounts of these impurities in general lead to a drop in performance of the catalysts of the type mentioned.

It is an object of the present invention to provide oxidation catalysts, especially for the gas phase oxidation of methacrolein to methacrylic acid, which, if industrial grades of methacrolein, and catalyst particle sizes conventionally used industrially in fixed bed reactions, are employed, guarantee high yields and a low formation of by-products even at high space velocities and over long operating periods.

We have found that this object is achieved by providing oxidation catalysts of the general formula $$Mo_{12}P_aW_bSb_cAs_dCu_eX_fO_x$$

where

X is one or more elements in the group comprising Nb, Fe, Mn, Sn and Cr,
a is 0.1-3,
b is 0.1-4,
c is >0-2,
d is 0-1,
e is 0-1,
d+e is >0-2,
f is 0-1.5,
e+f is 0-2 and
x is the number of oxygen atoms formally required to saturate the valencies of the other components.

The $NH_4^+$ ions which may or may not be present are, for formal reasons, not shown in the formula. The catalysts can contain other components in amounts which result from their natural presence in the raw materials employed, for example alkali metals such as potassium and sodium.

However, the concentration of the alkali metals should be less than 0.1, preferably less than 0.035, atom per 12 atoms of molybdenum, since the influence of the alkali metals tends to be detrimental.

As regards the exact composition, preferred oxidation catalysts of the above formula are those where
a is 0.5-2,
b is 0.5-3,
c is 0.2-1.5,
d is 0.01-0.5,
e is 0.01-0.5 and
f is 0-1.0, especially >0-1.

Of the components of the group X, Nb and/or iron, if desired in combination with a further component of this group, are preferred.

In general the catalysts are prepared by bringing together the compounds of the individual components in an aqueous medium, ie. in aqueous solution or suspension, under conditions which lead to formation of the phosphorus-containing heteropolyacids of molybdenum and tungsten or their salts, then drying and molding the product, and finally, advantageously, activating the product by calcining at an elevated temperature.

Examples of suitable sources of molybdenum and tungsten are molybdic acid, ammonium molybdate, phosphomolybdic acid and its ammonium salt, tungstic acid, ammonium tungstate, phosphotungstic acid and its ammonium salt. Though other compounds can also be employed, the above compounds are preferred, in particular the use of phosphotungstic acid as the tungsten source and of ammonium molybdate, molybdic acid and phosphomolybdic acid as the source of molybdenum. Arsenic is advantageously employed as an oxide or acid or as an ammonium salt of an acid. Various compounds can be employed as sources of phosphorus in addition to the heteropolyacids mentioned above, but phosphoric acid and its ammonium salts are preferred. The cationic elements can be employed, for example, in the form of the oxides, carbonates, nitrates, chlorides, fluorides, formates, oxalates or acetates. However, they are preferably employed in the form of the salts of the low molecular weight monocarboxylic acids and dicarboxylic acids. The presence, in the starting solution and during preparation, of organic compounds having a reducing action, especially of low molecular weight monocarboxylic acids, such as formic acid or acetic acid, dicarboxylic acids and hydroxycarboxylic acids, such as oxalic acid, tartaric acid, citric acid or their salts, preferably formic acid alone or in combination with the above acids, especially acetic acid, is in general advantageous. The carboxylic acids can be added in amounts of from 0.02 to 2 moles, preferably from 0.05 to 1.5 moles per mole of molybdenum. On the other hand, higher chloride ion concentrations can in some cases have a harmful effect on the catalysts. Accordingly, the amount of chloride ions in the starting solution should preferably be less than 0.3, especially less than 0.25, mole per mole of molybdenum.

The components can be combined at room temperature or at an elevated temperature. For example, the aqueous solutions or suspensions of molybdic acid, phosphoric acid, arsenic acid, antimony(III) oxide and copper oxide or copper salt can be mixed and subsequently refluxed, for example for from 2 to 24 hours. In another embodiment, the aqueous solutions of water-soluble compounds of the components, for example ammonium heptamolybdate, diammonium phosphate, diammonium arsenate or arsenic acid and antimony trichloride are mixed in hydrochloric acid solution or, preferably, in formic acid, tartaric acid, succinic acid or citric acid solution, at room temperature, the mixture is combined with the aqueous solution of, for example, phosphotungstic acid, and after addition of the cationic added components the mixture is dehydrated at an elevated temperature.

The dehydration or drying of the aqueous suspension of the components is in general effected by evaporation in a stirred kettle at below 140° C. or by spray drying at an exit temperature of from 80° to 140° C.

After having been dried, the mass obtained is generally milled to a particle size of from 200 to 1,200 μm and molded, if appropriate, after addition of conventional carriers, such as $SiO_2$ or aluminum oxides, with or without lubricants such as graphite, to give balls, tablets, rings or other shapes. These can then be calcined and/or activated in air, under nitrogen or in a slightly reducing atmosphere, at a low gas flow rate and at from 180° to 400° C., preferably from 220° to 380° C., especially from 320° to 360° C. The carriers can also be added during evaporation of the catalyst suspension, as a result of which the catalyst components are deposited on the carriers. Alternatively again, the dried and milled catalyst composition, without addition of carriers, can be calcined at the stated temperatures and then converted to moldings or be applied to carriers, especially to spherical carriers in the form of shells, in a conventional manner, for example by the methods disclosed in U.S. Pat. Nos. 4,305,843 and 4,297,247. After calcining, the catalytically active compositions have solely the structure of a heteropolyacid with defects, or of the salts of such an acid, with characteristic X-ray diffraction lines. The catalysts are particularly suitable for the gas phase oxidation of methacrolein to methacrylic acid under conventional conditions, especially if methacrolein prepared by condensing formaldehyde with propanal is used as the starting material.

In the gas phase oxidation of methacrolein, the oxidizing agent used is a gas mixture containing oxygen and steam, which is passed over the catalyst, generally in the form of a fixed catalyst bed. The process is generally carried out under pressures of from 1 to 5 bar, advantageously from 1 to 2.5 bar. In the process, the residence time of the methacrolein-containing gas mixtures is, based on standard conditions, generally from 0.5 to 5 sec.; residence times of from 1 to 3 sec. at from 200° to 340° C., especially from 220° to 320° C., are preferred. In addition to oxygen, methacrolein and steam the reaction gases in general contain inert gases, especially nitrogen; the oxygen is in general introduced as air but can also be employed as pure oxygen. Moreover, the reaction gas generally contains carbon oxides, especially if the reaction exit gas remaining after isolation of the methacrylic acid formed is recycled as a diluent, together with unconverted methacrolein, to the oxidation reaction.

In the reaction gas, the molar ratio of methacrolein:oxygen:water:inert gas is generally 1:1-6:1-20:4-50, preferably 1:1.5-4:2-10:6-30. The methacrylic acid can be isolated from the hot reaction exit gases in a conventional manner, generally by chilling with water.

The methacrolein can be obtained by various processes, for example by gas phase oxidation of tert.-butyl-alcohol, isobutylene or $C_4$ mixtures or by condensing propanal with formaldehyde. The use of the novel catalysts is particularly advantageous if the methacrolein employed has been prepared by condensing propionaldehyde with formaldehyde in the presence of salts of secondary amines or with aminals in the presence of acids in aqueous solution. Industrial grades prepared in this way are in general from 94 to 99% pure and in addition to unconverted propionaldehyde contain small amounts of organic amines, such as diethylamine or diethanolamine, methylpentenal and dimers of methacrolein. The purities mentioned are based on anhydrous crude methacrolein, but in practice the material can contain up to 3.5% by weight of water. If unconverted methacrolein and uncondensed reaction exit gases are recycled to the oxidation reaction, the synthesis gas mixture may also contain small amounts of very volatile by-products, such as carbon oxides or acrolein.

In industrial operation, the process is generally carried out in tube bundle reactors in which the catalyst is present in a fixed arrangement. To avoid local overheating, the catalyst activity can be modified so that it increases continuously, or in stages, in the direction of flow in the reaction tube. This can be achieved, for example, by diluting the catalyst with less active or even inactive catalyst or carrier moldings or by employing 2 or more catalysts differing in activity and/or selectivity. It is also possible to carry out the oxidation of methacrolein to methacrylic acid, according to the invention, in a fluidized bed, though fixed catalyst beds are preferred.

On working up the reaction gases, which can also be cooled indirectly before scrubbing with water, aqueous solutions of methacrylic acid are obtained, which may additionally contain small amounts of acetic acid, maleic acid and acrylic acid. The methacrylic acid can be extracted from the solutions obtained by means of suitable solvents, for example methyl methacrylate, in a conventional manner, and can either be directly esterified with an alkanol or be distilled out of the extract and separated from the by-products. The unconverted methacrolein can be distilled from the aqueous condensate or, for example, be stripped out with steam, and be recycled to the oxidation reaction.

The novel catalysts also exhibit a good activity and selectivity in other oxidation reactions, for example in the oxidation of acrolein to acrylic acid or in the oxidation of substituted toluene derivatives to substituted benzaldehydes and benzoic acids.

In the Examples which follow, 97–99% pure methacrolein is employed, which in addition to water and propionaldehyde contains small amounts of secondary amines and by-products of the synthesis of methacrolein from propanal and formaldehyde. Parts and percentages are by weight, unless stated otherwise. Parts by volume bear the same relation to parts by weight as that of the liter to the kilogram.

EXAMPLE 1

To an aqueous solution of 212 parts of ammonium heptamolybdate in 600 parts by volume of water were added successively a solution of 13.2 parts of diammonium phosphate and 1.3 parts of diarsenic pentoxide in 100 parts by volume of water, 22.6 parts of antimony(III) chloride in a mixture of 6 parts by volume of formic acid and 20 parts by volume of water, a solution of 19 parts of phosphotungstic acid in 50 parts by volume of water and, finally, a solution of 2.5 parts of copper(II) acetate in 100 parts by volume of water. The suspension was evaporated on a water bath at about 85° C. and the dry mass was milled to a particle size of less than 1.2 mm, mixed with 2% of graphite powder and pressed to give 3×3 mm tablets. The moldings were then heated for 6 hours at 355° C. The catalyst obtained had the formal composition $Mo_{12}W_{0.9}P_{1.09}Sb_1As_{0.1}Cu_{0.12}O_x$.

80 parts by volume of catalyst tablets were introduced into a reaction tube of 16 mm diameter, which was heated in a salt bath. A gas mixture of 3.3% by volume of methacrolein, 9.1% by volume of oxygen, 29.5% by volume of steam and 58.1% by volume of nitrogen was passed over the catalyst at a space velocity of 1,320 $h^{-1}$. After 7 days operation at a bath temperature of 318° C., the conversion was 94.3 mole %, the selectivity 85.8 mole % and the yield of methacrylic acid 80.9 mole %. After 10 days' operation, the conversion was 94.4 mole %, the selectivity was 90.5 mole % and the yield of methacrylic acid was 85.4 mole %. The yield of acetic acid by-product was 2.6 mole %. After 30 days' operation, the conversion was 94.1 mole %, the selectivity was 86.2 mole % and the yield of methacrylic acid was 81.1 mole %.

COMPARATIVE EXAMPLES (1A) Example 1 was repeated except that no antimony salt was added. Under the test conditions of Example 1, the optimum yield was achieved at a bath temperature of 280° C. Under these conditions the conversion was 75.5 mole %, the selectivity was 70.8 mole % and the yield of methacrylic acid was 53.4 mole %. The yield of acetic acid was 4.6 mole %.

(1B) Example 1 was repeated but neither the arsenic salt nor the copper salt was added. Under the test conditions of Example 1, and at a bath temperature of 300° C., which was the optimum in respect of methacrylic acid formation, the conversion was 92.8 mole %, the selectivity was 81 mole %, the yield of methacrylic acid was 75 mole % and the yield of acetic acid by-product was 4.6 mole %.

(1C) The preparation of the catalyst according to Example 1 was modified by omitting the addition of copper compound and arsenic compound and replacing the formic acid added by concentrated hydrochloric acid. Under the test conditions of Example 1, and at a bath temperature of 300° C., the conversion was 82.6 mole %, the selectivity was 77.4 mole % and the yield of methacrylic acid was 63.9 mole %. Acetic acid was formed in a yield of 6.5 mole %.

EXAMPLE 2

365 parts of phosphomolybdic acid and 48 parts of phosphotungstic acid were successively dissolved in 2,500 parts of water and a solution of 2.6 parts of arsenic pentoxide hydrate in 100 parts of water was added. The mixture was heated to 50° C. and 58.4 parts of antimony(III) oxide and a solution of 10 parts of copper(III) acetate in 200 parts of water were added. The mixture was heated to 90° C. and kept at this temperature for 2 hours. The water was then evaporated off on a water bath and the product was dried for 12 hours at 90° C. The residue obtained was comminuted, mixed with 2% of graphite and pressed to give 3×3 mm tablets. The tablets were calcined for 6 hours at 350° C.

80 parts by volume of the calcined catalyst tablets were tested under the conditions given in Example 1, at a bath temperature of 310° C. The conversion was 84 mole %, the selectivity was 84.5 mole % and the yield of methacrylic acid was 71 mole %.

EXAMPLES 3 TO 14

Following a procedure similar to Example 1, additional catalysts were prepared, with the modification that further added components were introduced, or arsenic or copper were not added, or the ratios of the components were changed. The catalysts were tested under the conditions of Example 1, with the exception of the bath temperature. The catalyst compositions and test conditions are summarized in Table 1. The added components were introduced in the following form: manganese (II)-acetate tetrahydrate, iron(II) oxalate, niobium pentoxide, ammonium chromate, tin(II) oxide, potassium nitrate, rubidium nitrate and cesium nitrate.

EXAMPLES 15 TO 17

Further catalysts were prepared and tested as in Example 1, except that the added formic acid was replaced by tartaric acid, citric acid or oxalic acid. The amounts of acid added and the test results are summarized in Table 2.

TABLE 1

| Example | Catalyst | Bath temperature °C. | Conversion mole % | Selectivity mole % | Yield mole % | after... days of operation |
|---|---|---|---|---|---|---|
| 3 | $Mo_{12}P_{1.18}W_{1.8}Sb_{1.2}As_{0.1}Cu_{0.25}$ | 319 | 93.8 | 83 | 77.9 | 12 |
| 4 | $Mo_{12}P_{1.1}W_{0.9}Sb_{0.2}As_{0.2}Cu_{0.05}$ | 314 | 92.1 | 85 | 78.3 | 8 |
| 5 | $Mo_{12}P_{1.1}W_{0.9}Sb_1Cu_{0.25}$ | 284 | 91.7 | 84.6 | 77.5 | 6 |
| 6 | $Mo_{12}P_{1.1}W_{0.9}Sb_1As_{0.2}$ | 302 | 89.6 | 81.3 | 72.8 | 10 |
| 7 | $Mo_{12}P_{1.1}W_{0.9}Sb_1As_{0.2}Cu_{0.1}Mn_{0.1}$ | 318 | 91.7 | 84.5 | 77.4 | 10 |
| 8 | $Mo_{12}P_{1.1}W_{0.9}Sb_1As_{0.2}Cu_{0.1}Nb_{0.4}$ | 324 | 95 | 87.2 | 82.8 | 7 |
| 9 | $Mo_{12}P_{1.1}W_{0.9}Sb_1As_{0.2}Cu_{0.1}Fe_{0.1}$ | 312 | 94.4 | 85.9 | 81.1 | 11 |

TABLE 1-continued

| Example | Catalyst | Bath temperature °C. | Conversion mole % | Selectivity mole % | Yield mole % | after ... days of operation |
|---|---|---|---|---|---|---|
| 10 | $Mo_{12}P_{1.1}W_{0.9}Sb_1As_{0.2}Cu_{0.1}Sn_{0.05}$ | 316 | 91.1 | 84.0 | 76.5 | 8 |
| 11 | $Mo_{12}P_{1.1}W_{0.9}Sb_1As_{0.2}Cu_{0.1}$ | 316 | 92.9 | 85.2 | 79.2 | 10 |
| 12 | $Mo_{12}P_{1.2}W_{1.8}Sb_1As_{0.2}Cu_{0.25}K_{0.03}$ | 319 | 95.6 | 81.9 | 78.3 | 7 |
| 13 | $Mo_{12}P_{1.1}W_{0.9}Sb_1As_{0.2}Cu_{0.25}Cs_{0.09}$ | 326 | 92.2 | 81.9 | 75.6 | 4 |
| 14 | $Mo_{12}P_{11}W_{0.9}Sb_1As_{0.2}Cu_{0.25}Rb_{0.03}$ | 319 | 91.5 | 83.5 | 76.4 | 7 |

TABLE 2

| Example | Additive | Moles per mole of Mo | Bath temperature [°C.] | Conversion [mole %] | Selectivity [mole %] | Yield [mole %] |
|---|---|---|---|---|---|---|
| 15 | Tartaric acid | 0.11 | 312 | 87.4 | 84.5 | 73.8 |
| 16 | Citric acid | 0.08 | 300 | 83.5 | 85.2 | 71.2 |
| 17 | Oxalic acid | 0.18 | 316 | 81 | 93.2 | 75.5 |

We claim:
1. An oxidation catalyst of the formula:

$$Mo_{12}P_aW_bSb_cAs_dCu_eX_fO_x$$

wherein X is Nb, Fe, Mn, or a mixture thereof, and wherein
a is 0.5–2, b is 0.5–3, c is 0.2–1.5, d is 0.01–0.5, e is 0.01–0.5 and f is 0–1.0, and wherein said catalyst further contains an alkali metal ion in an amount of less than 0.035 atoms per 12 atoms of molybdenum and wherein x is the number of oxygen atoms formally required to saturate the valencies of the other catalyst components.

2. The oxidation catalyst as claimed in claim 1, wherein f is >1.0.

3. The oxidation catalyst as claimed in claim 1, wherein X is niobium or iron or a mixture thereof.

* * * * *